United States Patent
Oden et al.

(10) Patent No.: US 9,063,061 B2
(45) Date of Patent: Jun. 23, 2015

(54) DETECTION OF AN ANOMALY IN A BIOLOGICAL MATERIAL

(75) Inventors: Erik Oden, Taby (SE); Ragnar Kullenberg, Oskarstrom (SE); Anders Ullberg, Aby (SE); Fredrik Danielsson, Ekero (SE)

(73) Assignee: MANTEX AB (SE)

( * ) Notice: Subject to any disclaimer, the term of this patent is extended or adjusted under 35 U.S.C. 154(b) by 210 days.

(21) Appl. No.: 13/519,494

(22) PCT Filed: Dec. 29, 2010

(86) PCT No.: PCT/EP2010/070840
§ 371 (c)(1), (2), (4) Date: Aug. 20, 2012

(87) PCT Pub. No.: WO2011/080295
PCT Pub. Date: Jul. 7, 2011

(65) Prior Publication Data
US 2013/0003925 A1    Jan. 3, 2013

(30) Foreign Application Priority Data
Dec. 29, 2009    (EP) .................................... 09180863

(51) Int. Cl.
G01N 23/08        (2006.01)
G01N 23/083       (2006.01)
G01N 33/46        (2006.01)

(52) U.S. Cl.
CPC .............. G01N 23/08 (2013.01); G01N 23/083 (2013.01); G01N 33/46 (2013.01)

(58) Field of Classification Search
CPC ..... G01N 5/02; G01N 521/25; G01N 521/59; G01N 521/8851; G01N 23/02; G01N 23/063; G01N 23/083; G01N 23/16; G01N 23/18; G01N 23/20083; G01N 33/46; G01N 2021/3129; G01N 2021/8663; G01N 2021/88; G01N 2021/8851; G01N 2021/892; G01B 15/025

USPC ............ 378/51, 53, 54, 55, 56, 58, 62, 83, 88
See application file for complete search history.

(56) References Cited

U.S. PATENT DOCUMENTS

| 3,452,193 A | * | 6/1969 | Petersen ......................... 378/53 |
| 5,809,104 A | * | 9/1998 | Kullenberg et al. ............ 378/54 |
| 6,151,379 A | | 11/2000 | Kullenberg et al. |

(Continued)

FOREIGN PATENT DOCUMENTS

| EP | 1484612 | 12/2004 |
| WO | 9735175 | 9/1997 |
| WO | 2010037820 | 4/2010 |

OTHER PUBLICATIONS

International Search Report for PCT/EP2010/070840, Completed by the European Patent Office on Jan. 25, 2011, 2 Pages.

Primary Examiner — Glen Kao
Assistant Examiner — Julio M Duarte-Carvajalino
(74) Attorney, Agent, or Firm — Brooks Kushman P.C.

(57) ABSTRACT

A method for detecting an anomaly in a biological material is disclosed, including the steps of: irradiating the biological material with electromagnetic radiation of at least two different energy levels; measuring the amount of radiation transmitted through the biological material; and determining, for each energy level, a transmission value. Before or after irradiation of the biological material, a reference material of a predetermined thickness is irradiated and the amount of radiation transmitted is determined. For each energy level, a transmission calibration reference value is determined and a calibrated transmission value is determined for the biological material and the calibration reference. A material value based on a relationship between the calibrated transmission value and the presence of an anomaly in the biological material is determined by comparing the determined and expected material values for the biological material. A corresponding apparatus is also disclosed.

15 Claims, 4 Drawing Sheets

(56) References Cited

U.S. PATENT DOCUMENTS

| | | | |
|---|---|---|---|
| 6,449,334 B1 * | 9/2002 | Mazess et al. | 378/53 |
| 8,467,496 B2 * | 6/2013 | Ullberg et al. | 378/53 |
| 2009/0262893 A1 * | 10/2009 | Stewart et al. | 378/62 |
| 2011/0176658 A1 | 7/2011 | Ullberg et al. | |

* cited by examiner

DETECTION OF AN ANOMALY IN A BIOLOGICAL MATERIAL

CROSS-REFERENCE TO RELATED APPLICATION

This application is the U.S. national phase of PCT Appln. No. PCT/EP2010/070840 filed on 29 Dec. 2010, which claims priority to EP Patent Application No. 09180863.4 filed on 29 Dec. 2009, the disclosures of which are incorporated in their entirety by reference herein.

TECHNICAL FIELD OF THE INVENTION

The present invention relates to a method and an apparatus for detecting an anomaly in a biological material, such as wood.

BACKGROUND

In the wood and pulp industry it is often desirable to be able to detect an anomaly in a biological material. The anomaly may be an organic anomaly, such as rot, insect attacks, knots, sap stain, or annual rings in wood. The anomaly may also be an inorganic object, such as stone, metal, or glass, present in the biological material.

Detection of organic anomalies may, for example, be useful to be able to sort out biological material of inferior quality to ensure that an end product meets a specified standard. Detection of inorganic objects present in the biological material, on the other hand, may be required in order to remove the inorganic object as it may otherwise damage machines for chopping, grinding or sorting the biological material and cause costly stops.

For the purpose of detecting metal or stone in a stream of wood-like material, it is previously known to allow electromagnetic radiation to penetrate the stream of wood-like material and thereafter to measure the intensity and calculate the amount of the original intensity that has been absorbed. Since the absorption coefficient typically is higher for metal or stone than for wood, an increased intensity absorption may indicate presence of stone or metal. An example of such a method and device is found in EP 1 484 612. This known method and device use radiation of one single wavelength, and the results are unpredictable. Typically, an intensity absorption threshold used to indicate the presence of stone or metal is either too high such that some inorganic objects are not detected which may result in damage to the machines and costly stops due to breakdowns, or, if the intensity absorption threshold is lowered in an attempt to avoid undetected inorganic objects, there tend to be a significant number of false alarms resulting in a large amount of short but unnecessary stops. Moreover, the sensitivity of this method is insufficient for detection of organic anomalies.

WO 97/35175 discloses a method for using radiation of several energy levels in order to distinguish between e.g. different types of material in wood, etc. However, this method is primarily intended to determine the quality of tree trunks and the like, and is neither intended nor suitable for monitoring e.g. pre-processed material in an industrial process.

There is therefore a need for a method and apparatus that may be conveniently used in an industrial process for reliably detecting anomalies in a biological material, such as pre-processed biological material.

SUMMARY OF THE INVENTION

It is therefore an object of the present invention to provide an improved method and apparatus for reliably detecting anomalies in a biological material, and in particular pre-processed biological material, which overcome or at least alleviate the above-discussed problems of the prior art.

This object is achieved by means of the invention as defined in the appended claims.

According to a first aspect of the invention there is provided a method for detecting an anomaly in a biological material, comprising the steps of: irradiating the biological material with electromagnetic radiation of at least two different energy levels; measuring the amount of radiation transmitted through the biological material at the energy levels; determining, for each energy level, a transmission value through the biological material based on the radiation through the biological material; irradiating a reference material of a predetermined thickness with electromagnetic radiation of the energy levels; measuring the amount of radiation transmitted through the reference material at the energy levels; determining, for each energy level, a calibration reference value based on the radiation transmitted through the reference material; determining, for each energy level, a calibrated transmission value based on a ratio between the determined transmission value through the biological material for the energy level and the determined calibration reference value for the energy level; determining a material value based on a relationship between the calibrated transmission value for the energy levels; and determining the presence of an anomaly in the biological material based on a comparison between the determined material value and an expected material value for the biological material.

The present invention is particularly useable for detecting anomalies in wood chips, but it may also be used for other forms of wood, as well as for other types of biological material, such as pulp, biomass fuel, etc. The invention is particularly useful for biological material in a pre-processed form, such as in a liquid state or in separated form, and preferably in the form of chips.

The anomaly may be an organic anomaly such as rot, insect attacks, knots, sap stain, or annual rings in wood. The anomaly may also be an inorganic anomaly such as, for example, stone, glass, or metals.

By determining the amount of radiation transmitted through the biological material at the two energy levels in relation to a calibration reference value it may be ensured that adequate calibration is always at hand. Air or aluminum may preferably be used as the reference material.

The present invention is based on the understanding that by determining the amount of radiation transmitted through the biological material in relation to a calibration reference value and using a relationship between electromagnetic radiation of at least two different energy levels transmitted through the biological material a more accurate and/or reliable measurement can be achieved. Further, compared to the e.g. the above-discussed method disclosed in WO 97/35175 by the same inventors, there is with the present invention also no need to determine the separate attenuation coefficients of the material. Instead, a relative measurement is obtained, which is much less sensitive to disturbances etc. Further, there is hereby also no need to determine the thickness of the material. Still further, the quotient analyzed by means of the present invention is more sensitive, and provides more useful information, than the single energies taken each on it own.

The at least two different energy levels are both preferably of X-ray radiation wavelengths. Further, the radiation of both the energy levels are preferably emitted from a single radiation source operating in the energy range 20-150 kVp. Here, kVp (Peak kilovoltage) denotes the maximum voltage applied across an X-ray tube. It determines the kinetic energy of the electrons accelerated in the X-ray tube and the peak energy of the X-ray emission spectrum. The actual voltage across the tube may fluctuate.

The irradiation of the sample of the biological material with electromagnetic radiation of at least two different energy levels preferably comprises a first irradiation with a first energy level, and a subsequent second irradiation with a second energy level. Alternatively, the radiation source may comprise two or several separate juxtaposed radiation tubes which radiate either simultaneously or sequentially. Preferably, the different wavelength radiation traverses the material to be measured along essentially the same path.

The method/apparatus according to the present invention is very well suited for use in online measurements along conveyor lines where material is transported, in pipe-lines, etc. However, it is also very useable for measuring a piece of wood, e.g. for determining the quality of timber, or for measuring samples of material arranged in sample containers, e.g. for sample testing in process industries, in field measurements, etc.

The material value may be based on a K-value for the biological material, the K-value being calculated as:

$$K = \frac{\ln(N_{01}/N_1)}{\ln(N_{02}/N_2)}$$

wherein $N_{01}$, $N_{02}$ are calibrated reference values for the transmission at the two energy levels and $N_1$, $N_2$ are the transmission values through the biological material at the energy levels, and presence of an anomaly in the biological material is determined based on a comparison between the calculated K-value and an expected K-value for the biological material. It has been found by the present inventors that the K-value is relatively stable for inorganic objects of a relatively small size. Consequently, an advantage with using the K-value is that inorganic objects of a relatively small size may be reliably detected. The expected K-value may be the K-value of the surrounding material. For example, if the K-value for a portion of the material has a deviation that exceeds a predetermined deviation (e.g. exceeds ±0.4) this may indicate an inorganic object. The expected K-value may also be a predetermined K-value range which is set during initialization. For example, the predetermined K-value may be below 2.0, above 1.5 or a range from 1.5 to 2.0. Alternatively, the K-value range may be determined by determining a K-value for the biological material at a moisture content which is typical in the monitored process (e.g. 30%) and setting the K-value range as this K-value plus/minus a predetermined deviation (e.g. ±0.4).

It is also possible to use two or more criteria at the same time, in order to e.g. distinguishing between different types of anomalies, or different quantities of anomalies. This may e.g. be used to initiate different types of alarms or actions depending on the type and seriousness of the anomalies.

According to an alternative embodiment the method may further comprise determination of moisture content of the biological material, wherein the expected material value for the biological material may be adaptive to the moisture content of the biological material. As the absorption coefficient of the biological material, and thus the K-value of the biological material, typically depends on the moisture content of the biological material, a more reliable detection of anomalies in the biological material may hereby be achieved.

The method may further comprise the use of an alarm signal for indicating that an anomaly has been detected. The alarm signal may automatically trigger stop of a monitored the process, and/or or alert an operator by an audible signal and/or a visual indicator, such as a blinking lamp.

The method may further comprise determination of a size of the anomaly. An advantage is that anomalies that are so small that they do not jeopardize the process may be ignored. Additionally or alternatively, anomalies of different nature, such as being of different materials and/or different sizes, may also be identified and treated differently. For example, less severe anomalies may be ignored or merely indicated in a log report, whereas more severe anomalies may issue an alarm, a stop of the material transportation and the like.

According to an embodiment, the biological material may be transported on a conveyor line, wherein the biological material is irradiated with electromagnetic radiation of at least two different energy levels in a plane substantially perpendicular to a direction of advancement of the conveyor line.

The amount of radiation transmitted through the biological material at the two energy levels may be determined for a plurality of radiation paths penetrating the biological material in the plane substantially perpendicular to the direction of advancement of said conveyor line. The radiation paths may preferably be substantially parallel to each other.

The conveyor line may have a width in a direction perpendicular to the direction of advancement, wherein the radiation paths may be distributed throughout the width of the conveyor line. An advantage is that all of the material that passes by may be efficiently monitored.

The size of the detected anomaly may be determined based on its transversal and longitudinal extension, wherein the transversal extension may be determined based on the number of radiation paths for which the determined material value deviates from the expected material value for the biological material, and the longitudinal extension may be determined based on the duration during which the determined material value deviates from the expected material value for the biological material.

The method may further comprise provision of an image visualizing the anomaly in the biological material, the visualization being based on the calculated K-value. For example, the K-values may be translated into a gray scale image where the tone of each pixel is based on a K-value. Thus, the visualization may be used for optical analysis of the anomalies, e. g. for determining the type and/or size of the anomaly that is at hand.

The amount of radiation transmitted through the biological material at the two energy levels may be determined for at least two radiation paths penetrating the biological material at different angles, thereby enabling study of the anomaly in multiple dimensions.

According to a second aspect of the invention there is provided an apparatus for detecting an anomaly in a biological material, comprising:

a radiation source for sequentially irradiating the biological material and a reference material with electromagnetic radiation of at least two different energy levels;

a detector for determining the amount of radiation transmitted through the biological material and the reference material at the two energy levels; and a processor adapted to identify presence of an anomaly in the biological material based on a comparison between a determined material value and a expected material value for the biological material, wherein the determined material value is based on a relationship between calibrated transmission values for the energy levels.

This aspect of the invention provides similar advantages as discussed above in relation to the first aspect.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DETAILED DESCRIPTION OF PREFERRED EMBODIMENTS

Figure 1:
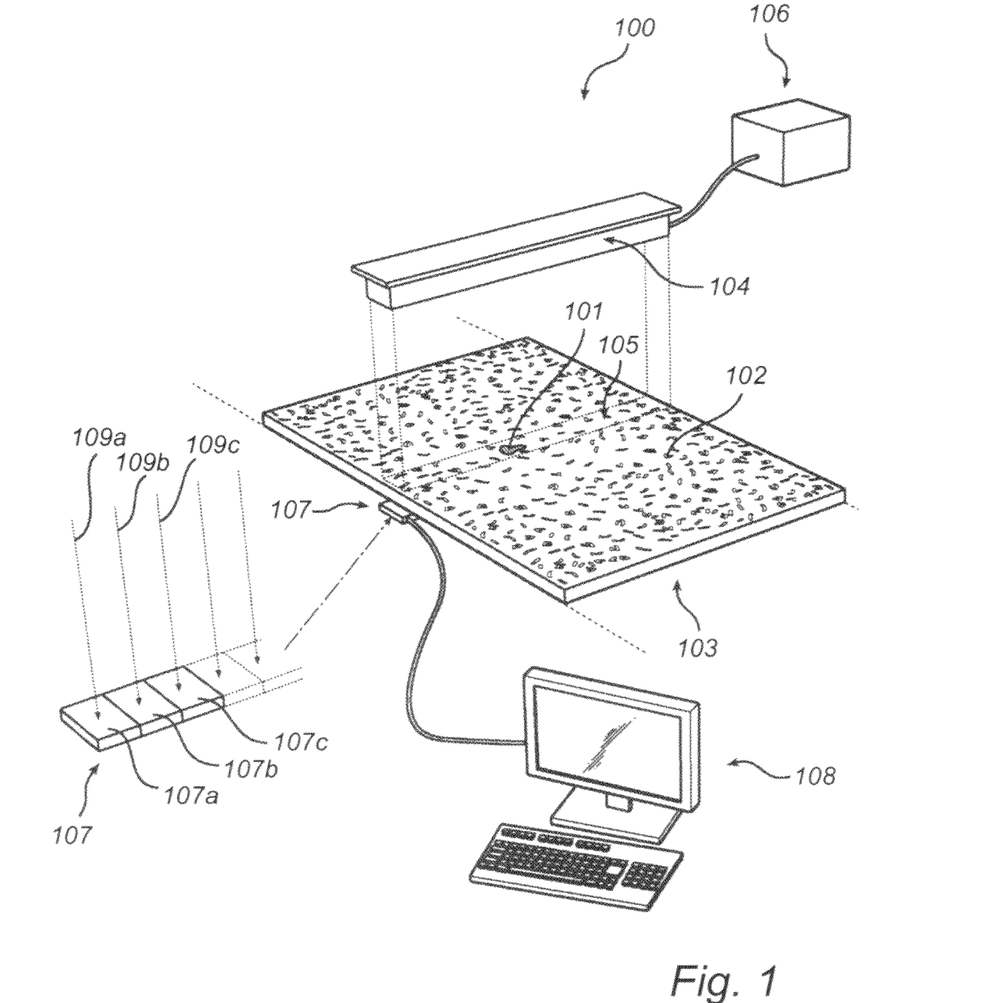
FIG. 1 schematically illustrates a measurement device for detecting an anomaly in a biological material transported on a conveyor line.

FIG. 1 schematically illustrates an embodiment of a measurement device 100 for detecting an anomaly 101 present in a biological material 102 transported on a conveyor line 103. The biological material 102 may typically be wood chips, whereas the anomaly may be an inorganic object such as stone, metal, or glass present in the biological material. In order to scan all of the material moved past the measurement device, the measurement device comprises a radiation source 104 adapted to irradiate a target area 105 that spans across the width of the conveyor line. The radiation source 104 is adapted to provide radiation of at least two different energy levels/wavelengths. Preferably, the radiation source is an X-ray tube for provision of X-ray radiation of two or more different wavelengths. Preferably, the X-ray tube operates in the range 20-150 kVp. The radiation source 104 is controlled by means of a controller 106.

Alternatively, the radiation source 104 may consist of two or several separate juxtaposed radiation tubes, wherein the juxtaposed radiation sources radiate the different wavelengths either simultaneously or sequentially. However, preferably the different wavelength radiation traverses the material to be measured along essentially the same path. When radiation of two (or more) wavelengths is emitted simultaneously from the radiation source the intensity of the two signals should preferably be measured individually. This may be effected directly by making provisions such that certain portions of the detector by filtration only measure radiation having a certain energy level while others measure other energy levels. It may also be effected by subsequent treatment of signals, allowing superimposed signals to be separated.

On the opposite side of the target area 105, a detector 107 is arranged to receive radiation transmitted through material located in the target area 105. The detector is preferably a semiconductor detector comprising a linear array of semiconductor detector areas 107a-c distributed across the width of the conveyor line. The number of detector areas may vary due to the size of anomalies that should be detected. Here it may be assumed that the linear array has 1024 detector areas (or pixels) per 20 cm. This allows inorganic objects with a size in the order of 1 mm to be identified. The detector 107 is connected to a control unit 108 with a processor, e.g. an ordinary personal computer. The control unit receives detection data from the detector through a suitable interface, such as through a USB port.

In operation, the radiation source 104 irradiates the material in the target area 105 with electromagnetic radiation of at least two different energy levels. This may be achieved by sequentially irradiating the material with radiation of a first wavelength, and radiation of a second wavelength, i.e. the radiation source initially emits rays having one wavelength and then, by altering the voltage across the radiation tube, a different wavelength. For each energy level, the amount of radiation transmitted through the material located in the target area 105 is measured on the opposite side of the target area 105 by the detector areas 107a-c of the detector, wherein each detector area 107a-c receives radiation that has penetrated the material 102 along a different radiation path 109a-c.

In order to get a reference value for calibration, it is preferred to measure a reference material. This can be achieved, for example, by measuring without any biological material present. Thus, in this case, a reference measurement is obtained with air as a reference material. Alternatively, the biological material may be replaced with a reference material with known properties, such as aluminum. The reference measurements may be obtained before measuring of the biological material, during initialization, or repeatedly during the process. Alternatively, reference measurements may be obtained by relocating the radiation source 104 and the detector 107 to a location next to the conveyor line such that the radiation passes through air only on its way from the radiation source to the detector. It is also possible to use additional radiation sources and detectors situated on one or both sides of the conveyor belt.

Based on these reference measurements, calibration reference values are determined as:

$$N_{01,02} = N_{Air1,2} \exp(\mu x)$$

where $N_{01}$ and $N_{02}$ are the calibration reference values for energy level 1 and 2, respectively, $N_{Air1}$ and $N_{Air2}$ are the detected transmission values after passage through the known distance of air, $\mu$ is the known attenuation coefficient for air ($cm^{-1}$) and x is the known distance of air (cm) that separates the radiation source and the detector.

A K-value for the material is determined for the radiation received by each detector area 107a-c. The K-value is calculated as:

$$K = \frac{\ln(N_{01}/N_1)}{\ln(N_{02}/N_2)}$$

wherein $N_{01}$, $N_{02}$ are the calibrated reference values for the transmission at the two energy levels and $N_1$, $N_2$ are the transmission values through the biological material at the energy levels.

Thereafter, presence of an anomaly 101 in the biological material is determined by the control unit 108 by comparing the calculated K-value for each detector area 107a-c with an expected K-value for the material. This may be achieved by determining whether a portion of the material in the target area has a K-value that deviates from the surrounding material with more than predetermined deviation, e.g. deviates from the surrounding material with more than ±0.4.

Alternatively, the expected K-value may be a predetermined K-value range which is experimentally determined and during initialization is stored in a database accessible by the control unit 108. Exemplary K-values for typical biological materials frequently used by the wood and pulp industry are specified in the below table.

| Organic substances | K-value (at 30% moisture content) |
| --- | --- |
| Pine | 1.71 |
| Spruce | 1.7 |
| Eucalyptus | 1.77 |
| Birch | 1.73 |
| Stump chips | 1.83 |
| Peat | 1.92 |

As a comparison, exemplary K-values for a few inorganic objects are specified in the below table.

| Inorganic substances | K-value |
| --- | --- |
| Stone | 2.2-2.7 |
| Glass | 2.1-2.5 |
| Brass | 2.3-2.5 |
| Aluminium | 2.0-2.2 |
| Steel | 1.1-1.3 |

The above-discussed K-values are related to specific voltages applied to the X-ray tube for generating the radiation at the two energy levels. If different voltages are used, the exact values for the K-value would naturally be different. However, the above-discussed principles underlying the present invention would still remain the same.

Figure 2:
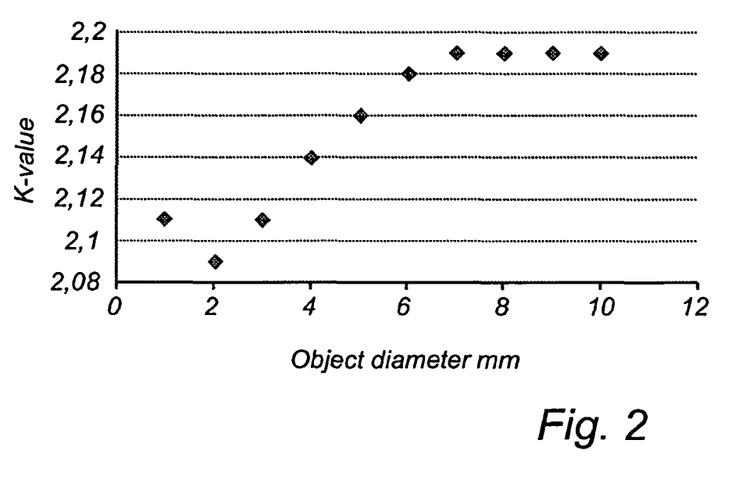
FIG. 2 is a graph showing how the K-value varies due to the diameter for a glass object.

Regarding the K-values for inorganic material it may be noted that these typically are stable also for relatively small inorganic objects, thereby allowing organic objects of a relatively small size to be reliably detected. This is exemplified in FIG. 2 which illustrates the K-value for objects of glass of different diameters. Here it appears that the K-value for glass is stable for a diameter above 6 mm.

From the above tables it appears that, to identify inorganic objects present in the biological material, the predetermined K-value range may preferably be set to a range from 1.5 to 2.0. Thus if the calculated K-value falls outside this range it is an indication that an inorganic object may be present in the biological material.

Alternatively, the predetermined K-value range may be defined as the K-value at 30% moisture content plus/minus a predetermined deviation (e.g. ±0.4).

Optionally, the reliability of the measurement device may be further improved by measuring the moisture content of the biological material and providing a predetermined K-value range adaptive to the moisture content. The moisture content may e.g. be estimated by the same measurements of radiation at two different energy levels, as is described in PCT-application with application number EP2009/062767 by the same applicant, said document hereby incorporated by reference.

As an inorganic object has been detected, its size is preferably determined. The size can be determined based on the transversal and longitudinal extension of the inorganic object. The transversal extension is here determined by the number of radiation paths for which the calculated K-value deviates from the predetermined expected K-value, i.e. the number of detector areas 107*a-c* for which the calculated K-value deviates from the predetermined expected K-value. The longitudinal extension of the inorganic object is here calculated from the duration during which the calculated K-value deviates from the predetermined expected K-value, and a known speed of the conveyor line.

When the detected inorganic object exceeds a predetermined minimum size, the control unit 108 provides an alarm signal that stops the monitored process and alerts an operator.

Optionally, the control unit 108 may provide an image of the portion of the biological material where the inorganic object was detected, allowing the operator to optically analyze the identified inorganic object. The image is preferably based on the calculated K-values. For example, the K-values may be used to render a gray scale image where the tone of each pixel is based on the corresponding K-value. If required, the identified inorganic object may then be removed from the biological material, before the process is resumed.

Figure 3A:
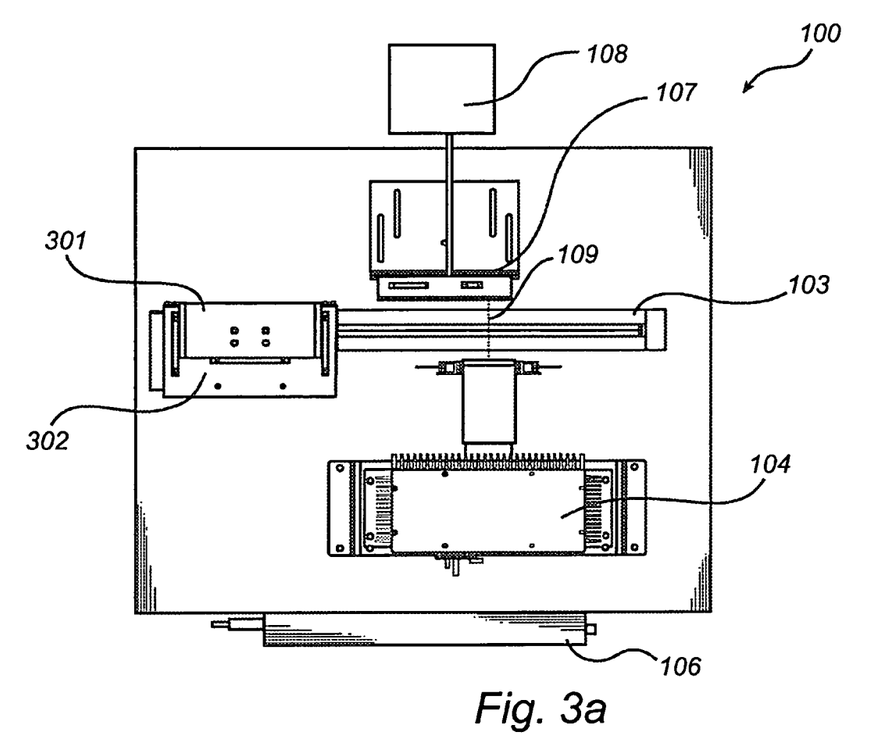
FIG. 3a-b schematically illustrates an embodiment of the invention where the material to be measured is arranged in a sample container.
Figure 3B:
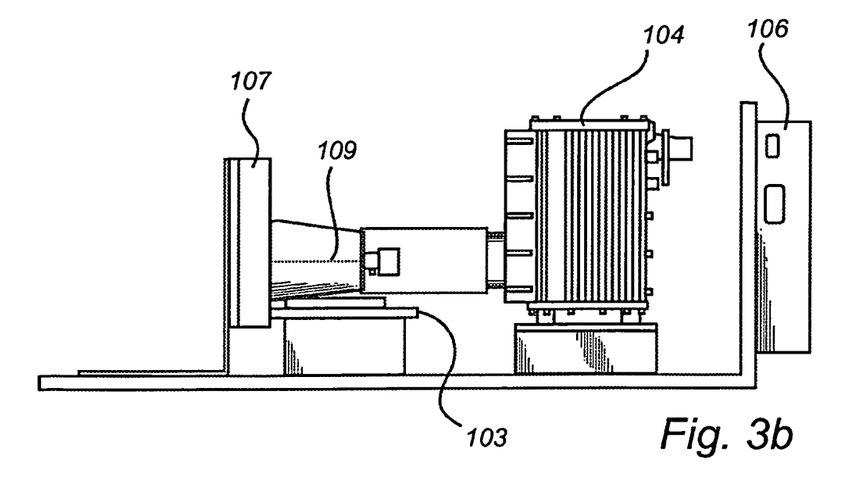

FIG. 3*a-b* schematically illustrates an alternative embodiment of a measurement device according the invention. The measurement device 100 comprises a radiation source 104 for irradiating a target area with at least two energy levels. The radiation source is controlled by means of a controller 106. A detector 107 is arranged on the opposite side of the target area. The detector is connected to a control unit 108 that receives detection data from the detector. In this embodiment, the material to be measured is arranged in a sample container 301. The sample container is then arranged on a carrier 302, which is movable in such a way that the sample container is moved through the target area, and thus through the radiation path 109. The carrier may e.g. be moved by means of a conveyor 103. However, other means for moving the carrier are also feasible, such as linear motors, screw arrangements, rail arrangements and the like.

During operation, the sample container is moved through the target area such that preferably all of the material in the sample container is scanned. At the first passage, the material sample is irradiated with radiation of a first wavelength, and in the second passage, during the return movement, with radiation of a second wavelength. In order to get a reference value for calibration, it is preferred to measure a reference material, preferably a predetermined amount of aluminum, at the beginning and end of the passage of the sample container.

Based on these reference measurements, calibration reference values are determined as:

$$N_{O1,O2} = N_{AI1,2} \exp(\mu x)$$

where $N_{O1}$ and $N_{O2}$ are the calibration reference values for energy level 1 and 2, respectively, $N_{AI1}$ and $N_{AI2}$ are the detected transmission values after passage through the known thickness of aluminum, $\mu$ is the known attenuation coefficient for aluminum (cm$^{-1}$) and x is the known thickness of the aluminum (cm).

Thereafter, a K-value for the biological material may be calculated as:

$$K = \frac{\ln(N_{O1}/N_1)}{\ln(N_{O2}/N_2)}$$

wherein $N_{O1}$, $N_{O2}$ are the calibrated reference values for the transmission at the two energy levels and $N_1$, $N_2$ are the transmission values through the biological material at the energy levels.

The presence of an inorganic object may then be determined by comparing the calculated K-value with a predetermined expected K-value for the biological material as has been previously been described for the embodiment illustrated in FIG. 1.

Figure 4:
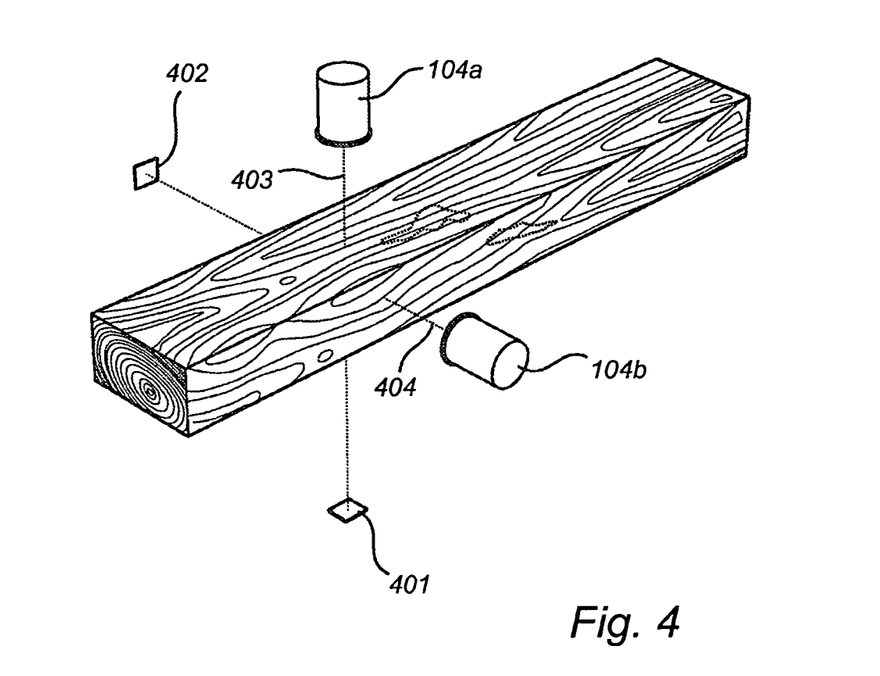
FIG. 4 schematically illustrates an embodiment where the material is irradiated at different angles to enable study of the material in multiple dimensions.

Although the above described embodiments describes detection of an inorganic object present in wood chip, the K-value may also be used to detect organic anomalies such as rot, insect attacks, knots, sap stain, or annual rings in a piece of wood, to be able to determine the quality of the wood. Furthermore, the quality of the wood can be studied in three dimensions by irradiating the material at different angles. FIG. 4 schematically illustrates how this can be achieved by using first 104a and second 104b radiation sources having associated first 401 and second 402 detectors. Here, the angle between a radiation path 403 of radiation output by the first radiation source and a radiation path 404 of radiation output by the second radiation is 90°. Note that each radiation source irradiates the material with at least two energy levels to be able to determine a K-value. Instead of using multiple radiation sources, the measured piece of wood may be rotated relative the radiation source in order to irradiate the material at different angles.

Specific embodiments of the invention have now been described. However, several alternatives are possible, as would be apparent for someone skilled in the art. For example, the radiation need not be X-ray, but other types of electromagnetic radiation may also be used.

Further, the radiation paths through the material may be arranged in various ways. For example, the paths may travel essentially along a single line, between a radiation source and a detector, or several detectors arranged overlapping or close to each other. However, the radiation paths may also be arranged along parallel lines, to form a "curtain" like measurement zone. It is also possible to use a plurality of non-parallel paths, e.g. extending from a single radiation source to a plurality of spread out detectors, to form a "fan shaped" measurement zone. Similarly, it would also be possible to use a plurality of separated radiation emerging points, and a single detection point, or the like. Many other types of geometries for the paths are also feasible.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A method for detecting an inorganic anomaly in a biological material, comprising steps of:
    irradiating the biological material with electromagnetic radiation of at least two different energy levels;
    measuring an amount of radiation transmitted through the biological material at the energy levels;
    determining, for each energy level, a transmission value through the biological material based on the radiation through the biological material;
    irradiating, before or after irradiation of the biological material, a reference material of a predetermined thickness with electromagnetic radiation of the energy levels;
    measuring the amount of radiation transmitted through the reference material at the energy levels;
    determining, for each energy level, a calibration reference value based on the radiation transmitted through the reference material;
    determining, for each energy level, a calibrated transmission value based on a ratio between the determined transmission value through the biological material for the energy level and the determined calibration reference value for the energy level;
    determining a material value based on a relationship between the calibrated transmission value the said energy levels; and
    determining presence of the inorganic anomaly in the biological material based on a comparison between the determined material value and an expected material value for the biological material,
    wherein the biological material is transported on a conveyor line,
    wherein the biological material is irradiated with electromagnetic radiation of at least two different energy levels in a plane substantially perpendicular to a direction of advancement of the conveyor line,
    wherein the amount of radiation transmitted through the biological material at the at least two energy levels is determined for a plurality of radiation paths penetrating the biological material in the plane substantially perpendicular to the direction of advancement of the conveyor line,
    wherein the conveyor line has a width in a direction perpendicular to the direction of advancement and wherein the radiation paths are distributed throughout the width of the conveyor line, and
    wherein the material value is based on a K-value for the biological material, the K-value being calculated as:

$$K = \frac{\ln(N_{01}/N_1)}{\ln(N_{02}/N_2)}$$

wherein $N_{01}$, $N_{02}$ are calibrated reference values for the transmission at the at least two different energy levels and $N_1$, $N_2$ are transmission values through the biological material at the energy levels, and presence of the inorganic anomaly in the biological material is determined based on a comparison between a calculated K-value and an expected K-value for the biological material.

2. The method of claim 1, further comprising determination of moisture content of the biological material, wherein the expected material value for the biological material is adapted to the moisture content of the biological material.

3. The method of claim 1, further comprising use of an alarm signal for indicating that the inorganic anomaly has been detected.

4. The method of claim 1, further comprising determination of a size of the inorganic anomaly.

5. The method of claim 1, wherein a size of the detected inorganic anomaly is determined based on its transversal and longitudinal extension, wherein the transversal extension is determined based on the number of radiation paths for which the determined material value deviates from the expected material value for the biological material, and the longitudinal extension is determined based on duration during which the determined material value deviates from the expected material value for the biological material.

6. The method of claim 1, further comprising provision of an image of the irradiated biological material visualizing the inorganic anomaly in the biological material, the visualization being based on the calculated K-value.

7. The method of claim 1, wherein the amount of radiation transmitted through the biological material at the two energy levels is determined for at least two radiation paths penetrating the biological material at different angles, thereby enabling study of the inorganic anomaly in multiple dimensions.

8. The method of claim 1, wherein the at least two different energy levels both are of X-ray radiation wavelengths.

9. The method of claim 1, wherein the radiation of the at least two different energy levels are emitted from a single radiation source operating in the energy range of about 20-150 kVp.

10. The apparatus of claim 1, wherein the inorganic anomaly is at least one of stone, glass, or metal.

11. An apparatus for detecting an inorganic anomaly in a biological material, comprising:
  a radiation source for sequentially irradiating the biological material and a reference material with electromagnetic radiation of at least two different energy levels;
  a detector for determining an amount of radiation transmitted through the biological material and the reference material at the two energy levels; and
  a processor adapted to identify presence of the inorganic anomaly in the biological material based on a comparison between a determined material value and an expected material value for the biological material, wherein the determined material value is based on a relationship between calibrated transmission values for the energy levels,
    wherein the material value is based on a K-value for the biological material, the K-value being calculated as:

$$K = \frac{\ln(N_{01}/N_1)}{\ln(N_{02}/N_2)}$$

wherein $N_{01}$, $N_{02}$ are calibrated reference values for the transmission at the at least two different energy levels and $N_1$, $N_2$ are transmission values through the biological material at the energy levels, and presence of the inorganic anomaly in the biological material is determined based on a comparison between a calculated K-value and an expected K-value for the biological material.

12. The method of claim 11. wherein the biological material is transported on a conveyor line,
  wherein the biological material is irradiated with electromagnetic radiation of the at least two different energy levels in a plane substantially perpendicular to a direction of advancement of the conveyor line,
  wherein the amount of radiation transmitted through the biological material at the at least two energy levels is determined for a plurality of radiation paths penetrating the biological material in the plane substantially perpendicular to the direction of advancement of the conveyor line, and
  wherein the conveyor line has a width in a direction perpendicular to the direction of advancement and wherein the radiation paths are distributed throughout the width of the conveyor line.

13. The method of claim 11, wherein the inorganic anomaly is at least one of stone, glass, or metal.

14. The method of claim 12, wherein the inorganic anomaly is at least one of stone, glass, or metal.

15. A method for detecting an inorganic anomaly, the inorganic anomaly being at least one of stone, glass, or metal, in a biological material, comprising steps of:
  irradiating the biological material with electromagnetic radiation of at least two different energy levels;
  measuring the amount of radiation transmitted through the biological material at the energy levels;
  determining, for each energy level, a transmission value through the biological material based on the radiation through the biological material;
  irradiating, before or after irradiation of the biological material, a reference material of a predetermined thickness with electromagnetic radiation of the energy levels;
  measuring the amount of radiation transmitted through said reference material at the energy levels;
  determining, for each energy level, a calibration reference value based on the radiation transmitted through the reference material;
  determining, for each energy level, a calibrated transmission value based on a ratio between the determined transmission value through the biological material for the energy level and the determined calibration reference value for the energy level;
  determining a material value based on a relationship between the calibrated transmission value for the energy levels; and
  determining presence of the inorganic anomaly in the biological material based on a comparison between the determined material value and an expected material value for the biological material,
    wherein the material value is based on a K-value for the biological material, the K-value being calculated as:

$$K = \frac{\ln(N_{01}/N_1)}{\ln(N_{02}/N_2)}$$

wherein $N_{01}$, $N_{02}$ are calibrated reference values for the transmission at the at least two different energy levels and $N_1$, $N_2$ are transmission values through the biological material at the energy levels, and presence of the inorganic anomaly in the biological material is determined based on a comparison between a calculated K-value and an expected K-value for the biological material.

* * * * *

UNITED STATES PATENT AND TRADEMARK OFFICE
CERTIFICATE OF CORRECTION

| | | |
|---|---|---|
| PATENT NO. | : 9,063,061 B2 | Page 1 of 1 |
| APPLICATION NO. | : 13/519494 | |
| DATED | : June 23, 2015 | |
| INVENTOR(S) | : Erik Oden et al. | |

It is certified that error appears in the above-identified patent and that said Letters Patent is hereby corrected as shown below:

In The Claims

Column 10, Line 4, Claim 1:

After "calibrated transmission value"
Delete "the said" and
Insert -- for the --.

Signed and Sealed this
Twenty-ninth Day of December, 2015

Michelle K. Lee
*Director of the United States Patent and Trademark Office*